(12) United States Patent
Yu et al.

(10) Patent No.: US 9,266,920 B2
(45) Date of Patent: Feb. 23, 2016

(54) PREPARATION METHOD OF DEGLYCOSYLATED GINSENOSIDES

(71) Applicants: Zer-Ran Yu, Chiayi (TW); Shuen-An Kang, Taichung (TW)

(72) Inventors: Zer-Ran Yu, Chiayi (TW); Po-Wen Yu, Chiayi (TW); Be-Jen Wang, Chiayi (TW)

(73) Assignees: Zer-Ran Yu, Chiayi (TW); Shuen-An Kang, Taichung (TW)

( * ) Notice: Subject to any disclaimer, the term of this patent is extended or adjusted under 35 U.S.C. 154(b) by 0 days.

(21) Appl. No.: 14/151,121

(22) Filed: Jan. 9, 2014

(65) Prior Publication Data

US 2015/0191504 A1 Jul. 9, 2015

(51) Int. Cl.
*C07J 9/00* (2006.01)

(52) U.S. Cl.
CPC .......................................... *C07J 9/00* (2013.01)

(58) Field of Classification Search
CPC .................................... C07J 75/00; C07J 9/00
See application file for complete search history.

(56) References Cited

U.S. PATENT DOCUMENTS

2007/0014912 A1* 1/2007 Mazza et al. ................. 426/615

FOREIGN PATENT DOCUMENTS

CN 102415525 A * 4/2012
KR WO 2011059265 A * 5/2011

OTHER PUBLICATIONS

Sharif et al, Journal of Food Engineering, Experimental Design of Supercritical Fluid Extraction—A Review, 2014, 124, pp. 105-116.*
Wood, Masters Thesis, The University of Western Ontario, Extraction of Ginsenosides from North American Ginseng Using Supercritical Fluids, 2005, pp. i-151.*

* cited by examiner

*Primary Examiner* — Paul A Zucker
(74) *Attorney, Agent, or Firm* — Ming Chow; Sinorica, LLC

(57) ABSTRACT

The present invention provides a preparation method of deglycosylated ginsenosides, which uses the supercritical fluid technology to conduct the deglycosylation of ginsenosides extract in supercritical solvent under preset pressure and temperature conditions. Under the same operational conditions, the deglycosylated ginsenosides extract and solvent at supercritical state are input into an adsorption tank at the preset volume flow rate ratio for the adsorption of ginsenosides. Then, the adsorbed ginsenosides are applied with gradient eluent by using the ethanol solution. Finally, the pressure is lowered for the separation and purification of ginsenosides to get the deglycosylated ginsenosides of high concentration.

4 Claims, 4 Drawing Sheets

PREPARATION METHOD OF DEGLYCOSYLATED GINSENOSIDES

BACKGROUND OF INVENTION

1. Field of the Invention

The present invention relates generally to a ginseng extraction technology, and more particularly to a preparation method of deglycosylated ginsenosides.

2. Description of Related Art

Ginseng is the most common traditional medicine used in China, Korea, Japan and other Asian nations. Its major active components are ginsenosides. Its structure is some glycosides compounds bonded by aglycone skeletons containing protopanaxadiol (PPD) or protopanaxatriol (PPT). The common PPD structured ginsenosides include Rb1, Rb2, Rc, Rd; PPT structured ginsenosides are Rg1, Re.

Ginsenosides have the pharmacological effects of improving human nervous system, blood glucose, blood lipids, and blood pressure, and functions of promoting the body strength, memory, anti-oxidation, anti-aging, immunity, anti-cancer and sexuality. After the oral administration of ginseng, its ingredients can almost not be decomposed by gastric acid or liver enzymes, and thus the bio-absorption rate is very low around 0.1-3.7%. The conventional ginsenosides deglycosylation is either by the steam-heated drying method or hydrolysis of the glycosylated structure of ginsenosides by the microbial intestinal bacteria or β-glycosidase. The fresh peeled Korean ginseng is steam-heated to produce deglycosylated Rg3 and Rh2 ginsenosides. Although the product has the aforementioned body strengthening and pharmacological effects, the ginseng is brown in color and tastes bitter. Its ingredients will be damaged by the heat, and the price is high. Besides, only its main root can be used in processing, its leaves and fruits cannot be processed. Ginsenosides can also be deglycosylated by β-glycosidase from the intestinal bacteria. The glycosides of ginsenosides after hydrolysis can promote the absorption and utility rate of ginsenosides. However, 100-1000 times solvents are needed for the deglycosylation by β-glycosidase. After the reaction, complicated process, including concentration, separation, and purification steps, should be conducted. Moreover, the bacterial sources and enzyme activity should be taken into consideration, and thus the method limited the application of commercials.

SUMMARY OF THE INVENTION

The primary objective of the present invention is to provide a preparation method of deglycosylated ginsenosides. By using the safe and non-toxic solvent at the supercritical state, coupled with physical methods including high pressure and low temperature reaction method, and the low pressure and low temperature separation method, we can prepare the deglycosylated ginsenosides without using complicated solvent removal, concentration and separation procedures or solvent residual. The method is free of safety concerns, environmental friendly, and safe. Moreover, the solvent at the critical state can be reused; therefore, it is of great practical value.

Hence, for the aforementioned purposes, the present invention is to provide a preparation method of deglycosylated ginsenosides, which uses the supercritical fluid technology, under the preset operational conditions of pressure, temperature and flow rate, to conduct the deglycosylated reaction of the ginsenosides extracts by using the solvent at the supercritical state. Then, under the same operational conditions, the solvent at the supercritical state of preset flow rate is used to adsorb the ginsenosides from the deglycosylated ginsenosides extracts. Next, the adsorbed ginsenosides are gradually separate and purified by the ethanol solution according to gradient eluent to get deglycosylated ginsenosides of high concentration.

DETAILED DESCRIPTION OF THE INVENTION

Figure 1:
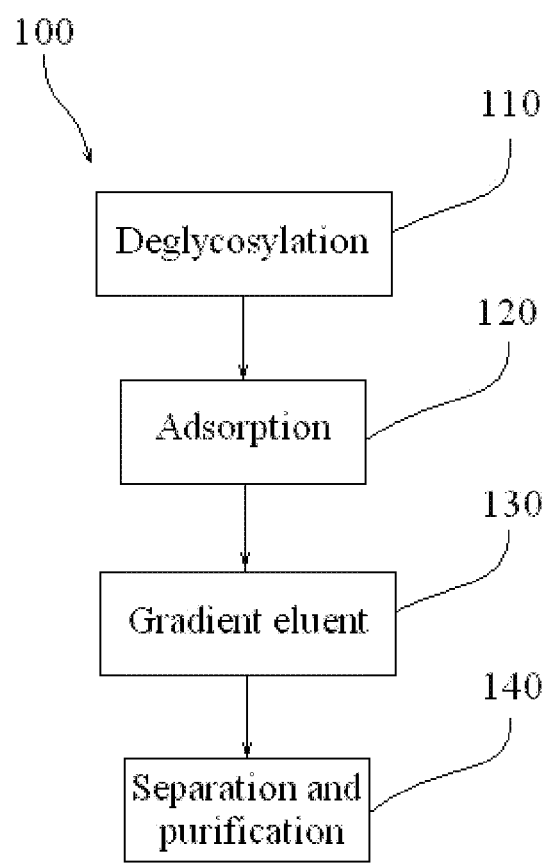
FIG. 1 is a flow chart of a preferred embodiment of the present invention.

We elaborate on the present invention with an embodiment and diagrams as follows:

Referring to FIG. 1, the present preparation method of deglycosylated ginsenosides 100 is to take advantage of the supercritical fluid technology to implement the following steps:

The first step of the present invention is deglycosylation 110: under the operational conditions of pressure at 20-30 MPa (for example, 20, 22, 24, 26, 28, 30 MPa), and temperature 40-60 degree (for example, 40, 50, 60 degree), the ginsenosides extract and the solvent at supercritical state ($CO_2$ supercritical fluid) are input at the preset volume flow rate ratio of 1: 60~100 into the reaction vessel for deglycosylation reaction for about an hour. The reaction vessel is a stainless steel vessel of radius at 0.125 m and height at 1 m filled with 0.24 inch stainless steel single pieces produced by American Canon Company.

The second step of the present invention is adsorption 120: under the aforementioned operational conditions (pressure 20-30 MPa and temperature 40-60 degree), the deglycosylated ginsenosides extract and the solvent at the supercritical state is input into the adsorption tank at the preset volumetric flow rate of 1: 60-100. The adsorption tank is a stainless steel tank of radius at 0.125 m and height at 1 m filled with adsorbents that can adsorb ginsenosides such as Silica gel, Sephadex or Resin.

The third step of the present invention is the gradient eluent 130: after ginsenosides being adsorbed by the adsorption tank, the ethanol solution eluents gradient from 20% ethanol to 80% ethanol.

The final step of the present invention is the separation and purification 140: the pressure is lowered to 10-20 MPa (for example, 10, 12, 14, 16, 18, 20 MPa), the supercritical solvent and ginsenosides are separated and purified to get the deglycosylated ginsenosides of high concentration. The solvent at the supercritical state can be recycled and reused.

Figure 2:
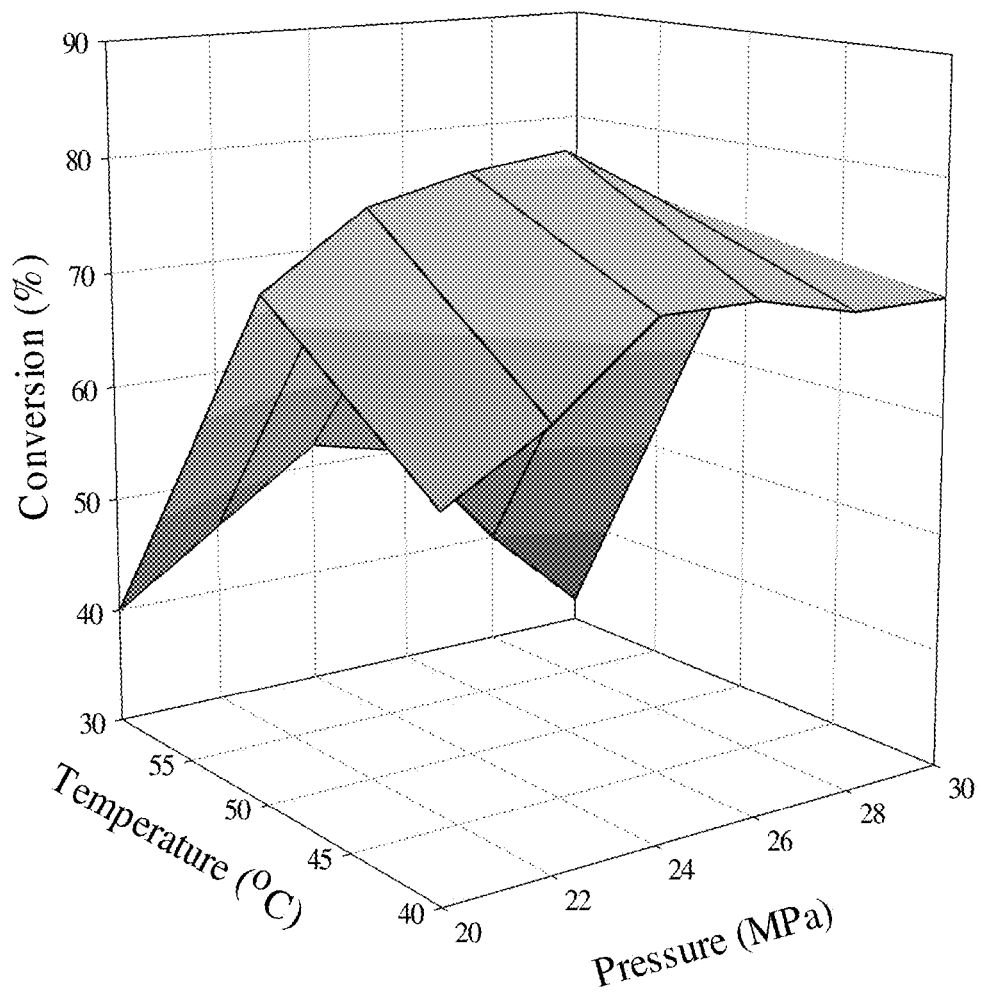
FIG. 2 is a diagram, showing the relationship of pressure, temperature and conversion.
Figure 3:
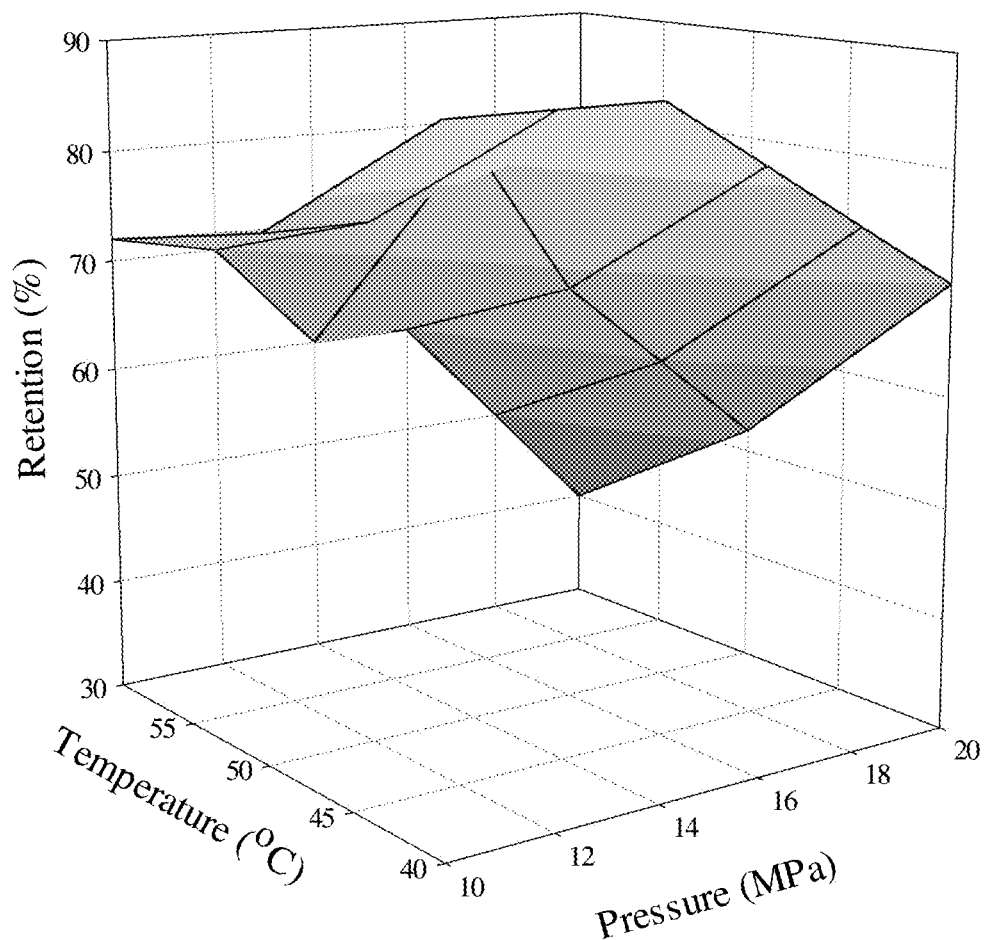
FIG. 3 is a diagram, showing the relationship of pressure, temperature and retention.
Figure 4:
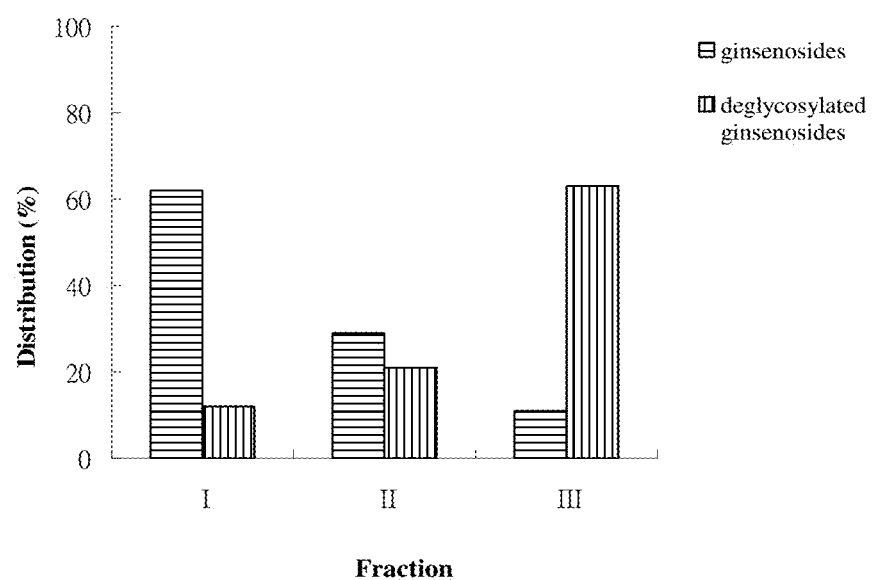
FIG. 4 is a diagram, showing the relationship of fraction and distribution of the ginsenosides and deglycosylated ginsenosides.

The aforementioned method is implemented by different operational conditions (change pressure and temperature) to get data of conversion and separation retention of ginsenosides deglycosylation and assess the optimal reaction conditions:

It can be learnt from the reaction conversion (%) as shown in FIG. 2, when the pressure is 24-26 MPa and the temperature is 50 degree, it can reach the 80% ginsenosides conversion, and thus is the most optimal operational condition. It is mainly because the solvent at the supercritical state of high pressure has high solubility and mass transfer rate. Therefore, it can replace the use of a large number of organic solvents in deglycosylation reaction for the hydrolysis of the glycosylated structure of ginsenosides. The supercritical fluid uses low temperature, low viscosity and high density to increase the contact opportunity of reactants and thus to speed up the deglycosylation. Under the supercritical $CO_2$ high pressure and low temperature operational conditions, it can overcome the shortcoming of using a large amount of organic solvents in the conventional method of microorganism and enzyme. By rapidly changing temperature and lowering pressure, the deglycosylated ginsenosides and unreacted materials can be physically separated. According to the analysis of the retention (%) as shown in FIG. 3, the most optimal separation conditions are: pressure at 10~12 MPa and temperature at 40 degree mainly because the separation mechanism can easily separate the reactants and supercritical $CO_2$, which can be recycled and reused, at low pressure and low temperature. Moreover, under the most optimal deglycosylation reaction and separation conditions, the ginsenosides extract during the preparation, reaction and separation in the supercritical $CO_2$ can be divided into I, II and III fractions as shown in FIG. 4. By analyzing the contents of deglycosylated ginsenosides (namely, products) and unreacted ginsenosides, we find about 62% of unreacted ginsenosides are retained in fraction I. By comparison, about 66% of the reaction products, namely, the deglycosylated ginsenosides are retained in fraction III.

The preparation method of the deglycosylated ginsenosides uses the safe and non-toxic supercritical solvent (supercritical $CO_2$), coupled with physical methods of high pressure and low temperature (namely, deglycosylation reaction at supercritical $CO_2$, which exhibits high solubility, low viscosity and high mass transfer efficiency), and the low pressure and low temperature physical method of separation (the method to separate the product and the supercritical solvent in lowered pressure and changed temperature) can be used to prepare the deglycosylated ginsenosides without the complicated procedures for solvent removal and concentration and safety concerns such as solvent residual. It is safe and environmentally friendly, and the solvent at the supercritical state can be recycled. By comparison, the conventional steam-heating procedure changes taste and smell, and the content of deglycosylated ginsenosides is about 1~2%. Moreover, the deglycosylation by hydrolysis of organic solvents and intestinal microorganism or enzyme has the disadvantage of safety concern. Therefore, the present invention is of obvious practical value.

What is claimed is:

1. A preparation method of deglycosylated ginsenosides, which uses the supercritical fluid technology to implement the following steps:
    deglycosylation: under the operational conditions of pressure at 20-30 MPa and temperature at 40-60° C., ginsenosides extract and a supercritical solvent is input into a reaction tank at the preset volume flow rate ratio of 1:60~100 for deglycosylation, wherein the supercritical solvent is a carbon dioxide fluid at supercritical state, and the reaction tank is a stainless steel tank filled with a plurality of stainless steel pieces;
    adsorption: under the same operational conditions as the above, the deglycosylated ginsenosides extract and solvent at the supercritical state are input into the adsorption tank at the preset volume flow rate ratio to adsorb the deglycosylated ginsenosides, wherein the adsorption tank is a stainless steel tank filled with the adsorbents selected from the group consisting of Silica gel, Sephadex, Resin and a combination thereof;
    gradient elution: ethanol solution is used for the gradient elution of the ginsenosides in the adsorption tank for separation and purification: the pressure is lowered to 10-20 MPa, the solvents at the supercritical state and the deglycosylated ginsenosides are separated and purified to get the deglycosylated ginsenosides of high concentration, wherein operation conditions for separation and purification comprise a pressure at 10~12 MPa and a temperature at 40° C.

2. The method defined in claim 1, wherein, in the deglycosylation step, the operations condition of the deglycosylation reaction is: pressure at 24~26 MPa and temperature at 50° C.

3. The method defined in claim 1, wherein, in the adsorption step, the adsorption tank is filled with adsorbents that can adsorb deglycosylated ginsenosides.

4. The method defined in claim 1, wherein, in the gradient elution step, the ethanol solution comprises from 20% ethanol solution to 80% ethanol solution.

* * * * *